(12) United States Patent  
DiUbaldi et al.

(10) Patent No.: US 8,897,885 B2  
(45) Date of Patent: Nov. 25, 2014

(54) OPTIMIZING THE STIMULUS CURRENT IN A SURFACE BASED STIMULATION DEVICE

(75) Inventors: Anthony DiUbaldi, Jackson, NJ (US); Stephen Wahlgren, Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 1298 days.

(21) Appl. No.: 12/317,193

(22) Filed: Dec. 19, 2008

(65) Prior Publication Data

US 2010/0161001 A1 Jun. 24, 2010

(51) Int. Cl.
*A61N 1/00* (2006.01)
*A61N 1/36* (2006.01)

(52) U.S. Cl.
CPC ................. *A61N 1/36014* (2013.01)
USPC .......... 607/62; 607/7; 607/8; 607/28; 607/46; 607/48; 607/49

(58) Field of Classification Search
USPC ............. 607/7, 8, 28, 46, 48, 49, 62
See application file for complete search history.

(56) References Cited

U.S. PATENT DOCUMENTS

| 5,476,481 A | 12/1995 | Schoendorf |
| 5,725,563 A | 3/1998 | Klotz |
| 2004/0088011 A1 * | 5/2004 | Snyder et al. ............ 607/5 |
| 2005/0277998 A1 | 12/2005 | Tracey et al. |
| 2007/0185541 A1 | 8/2007 | DiUbaldi et al. |
| 2008/0177342 A1 | 7/2008 | Snyder et al. |

FOREIGN PATENT DOCUMENTS

| JP | 8-508897 | 9/1996 |
| JP | 2000-288100 | 10/2000 |
| JP | 2001-245992 | 9/2001 |
| JP | 2006-504462 | 2/2006 |
| JP | 2008-534107 | 8/2008 |
| WO | WO 90/14127 A1 | 11/1990 |
| WO | WO 2005/002663 A2 | 1/2005 |

* cited by examiner

*Primary Examiner* — Michael Kahelin
*Assistant Examiner* — Mallika D Fairchild
(74) *Attorney, Agent, or Firm* — Cohen & Hildebrand, PLLC (57) ABSTRACT

A method and associated stimulation device for ensuring firing of an action potential in an intended physiological target activated by a stimulus pulse generated by an electrode of a non-invasive surface based stimulation device irrespective of skin-to-electrode impedance by: (i) increasing internal impedance of the stimulation device so as to widen a Chronaxie time period thereby ensuring firing of the action potential of the intended physiological target irrespective of the skin-to-electrode impedance; and/or (ii) generating a stimulation waveform that optimizes a non-zero average current (e.g., non-zero slope of the envelope of the stimulation waveform) during preferably substantially the entire current decay of the stimulus pulse.

15 Claims, 8 Drawing Sheets

OPTIMIZING THE STIMULUS CURRENT IN A SURFACE BASED STIMULATION DEVICE

BACKGROUND OF THE INVENTION

1. Field of the Invention

The present invention is directed to an improved surface based stimulation device that optimizes the stimulus current delivered while minimizing its duration resulting in higher efficiency and minimum power consumption.

2. Description of Related Art

Figure 1:
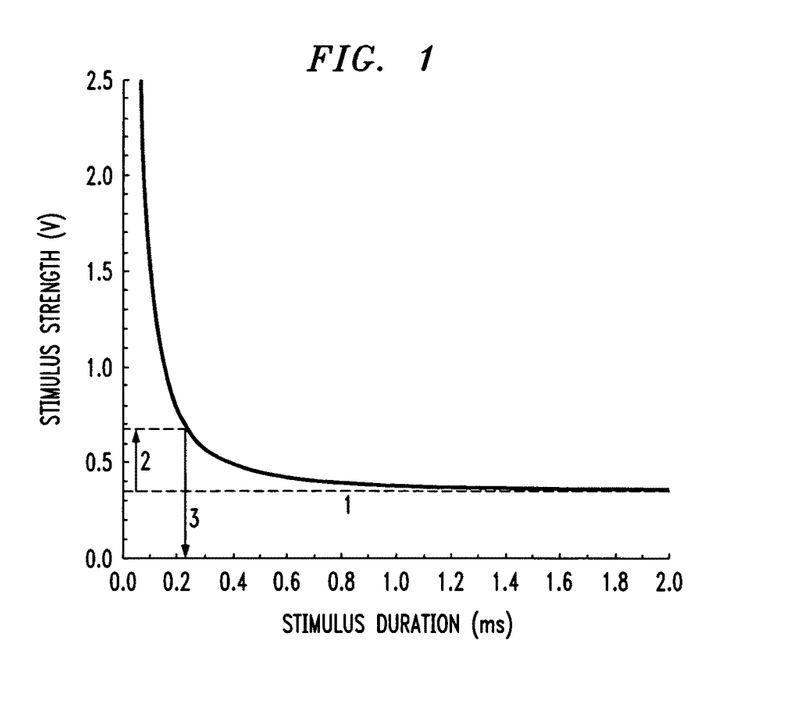
FIG. 1 is an exemplary strength—duration curve for stimulation of tissue.

A nerve cell can be excited externally by increasing the electrical charge within the nerve, thus increasing the membrane potential inside the nerve with respect to the surrounding extracellular fluid. U.S. patent application Ser. No. 11/146,522, filed on Jun. 7, 2005 and assigned to the same assignee as the present application, discloses an external transdermal nerve stimulation patch. This is but one example of a surface based stimulation device. The fundamental feature of the nervous system, i.e., its ability to generate and conduct electrical impulses, can take the form of action potentials (AP), which are defined as a single electrical impulse passing down an axon or fiber. This action potential (sometimes also referred to as a nerve impulse or spike) is an "all or nothing" phenomenon. Rheobase is the minimal electrical current of infinite duration (practically, a few hundred milliseconds) that results in an action potential. In addition, to a minimum intensity there is also a minimum amount of time necessary to excite the nerve. The minimum time referred to as Chronaxie is a duration of time that produces a response when the nerve is stimulated at twice the Rheobase strength. If either the stimulation time or stimulation intensity of the stimulation signal is not sufficient, the nerve will not fire an action potential. An exemplary strength-duration curve for excitable tissue shown in FIG. 1 denotes the Rheobase by reference element "1" and has a value of 0.25 V while the Chronaxie is represented by reference element "3" and has a value of approximately 0.23 ms.

When an external electrical stimulus is applied transcutaneously the complex impedance of the skin can alter the stimulus current. For example, if the capacitance of the skin increases, the amplitude of the stimulation signal may be sufficient to excite a nerve, however, an adequate amount of time may be lacking to fire the action potential. This is known as current decay. When a DC current is applied to the surface of the skin, a decay in current is observed until the net current is zero. Typically, this takes approximately 600 microseconds.

It is therefore desirable to develop an improved method and system that adjusts for changing impedance of the skin or decay in current.

SUMMARY OF THE INVENTION

An aspect of the present invention is directed to a system and method for widening or increasing the current decay to insure that the action potential will fire without increasing the amplitude or strength of the stimulation signal.

Another aspect of the present invention relates to a system and method for increasing the time allotted to the stimulus signal to fire the action potential and therefore prolong the decay in the current by adding an in-line series impedance on the electrode interface side.

Still another aspect of the present invention is directed to a system and method for increasing the time allotted to the stimulus signal to fire the action potential by employing a stimulus waveform envelope having a non-zero slope or rate of change at least during substantially the duration of current decay so that the average current is non-zero.

The present invention is directed to a method and associated stimulation device for ensuring firing of an action potential in an intended physiological target activated by a stimulus pulse generated by an electrode of a non-invasive surface based stimulation device irrespective of skin-to-electrode impedance by: (i) increasing internal impedance of the stimulation device so as to widen a Chronaxie time period thereby ensuring firing of the action potential of the intended physiological target irrespective of the skin-to-electrode impedance; and/or (ii) generating a stimulation waveform that optimizes a non-zero average current (e.g., non-zero slope of the envelope of the stimulation waveform) during preferably substantially the entire current decay of the stimulus pulse.

One particular aspect of the present invention is directed to a method for ensuring firing of an action potential in an intended physiological target activated by a stimulus pulse generated by an electrode of a non-invasive surface based stimulation device irrespective of skin-to-electrode impedance. This is accomplished by increasing an internal impedance of the stimulation device. The stimulus pulse is generated by the electrode. Accordingly, the increased internal impedance widens a Chronaxie time period thereby ensuring firing of the action potential of the intended physiological target irrespective of the skin-to-electrode impedance.

Another specific aspect of the present invention is directed to a stimulation device for realizing the method described in the preceding paragraph. The stimulation device includes a waveform generator for producing a stimulation waveform. An electrode is electrically connected to receive the stimulation waveform and produce a stimulus pulse. A resistor in series with the electrode is provided for increasing internal impedance of the stimulation device, wherein the increased internal impedance widens a Chronaxie time period so as to ensure firing of the action potential of the intended physiological target irrespective of the skin-to-electrode impedance.

Still another particular aspect of the present invention is directed to a method for ensuring firing of an action potential in an intended physiological target activated by a stimulus pulse generated by an electrode of a non-invasive surface based stimulation device irrespective of skin-to-electrode impedance. A stimulation waveform is generated that optimizes a non-zero average current (e.g., non-zero slope of the envelope of the stimulation waveform) during current decay of the stimulus pulse. The stimulus pulse is produced using the electrode that receives as input the stimulation waveform.

Yet another aspect of the present invention is directed to a stimulation device for realizing the method described in the preceding paragraph. The stimulation device includes a waveform generator for producing a stimulation waveform that optimizes a non-zero average current during current decay of the stimulus pulse. An electrode receives as input the stimulation waveform and generates the stimulus pulse.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

The present inventive system and method is an improvement for a non-invasive surface based stimulation device wherein an electrode is positioned proximate or in direct contact with the surface of the skin to externally stimulate a physiologic target, e.g., nerve or tissue to be treated. When an electrical stimulus is applied through the skin using external electrodes the complex impedance of the skin can alter the stimulus current. The impedance of the skin is changing constantly and is dependent on numerous factors. For instance, skin impedance gradually rises with advancing age, and females tend to show higher values then males. A significant correlation has been documented between the percentage decrease in skin impedance in response to strain on the joint such as during standing, bending, squatting, walking on a flat floor, and ascending/descending stairs. In addition, skin temperature, presence of hair and skin type also contribute to changes in impedance. If the impedance of the skin alters the stimulus current so that the amount of time needed to excite the nerve (Chronaxie) is not reached, the nerve will not be stimulated (i.e., the action potential will not be fired) and the stimulation device will therefore not be effective in treating the condition intended to be treated.

Figure 2:
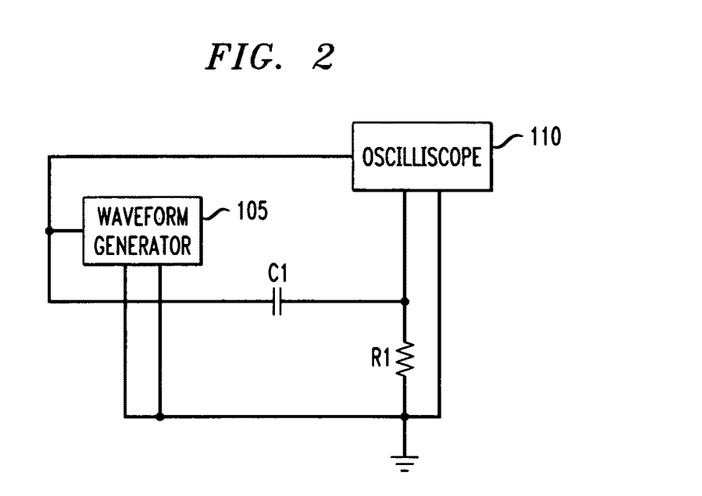
FIG. 2 is an exemplary schematic stimulation circuit simulating the skin to electrode interface and observing the differentiation current.

Therefore, a minimum stimulus duration is required to activate or fire the action potential. However, when the stimulus is provided via transcutaneous electrodes, the complex impedance of the skin can alter the stimulus current. The effect of the impedance at the electrode to skin interface may be approximated as a differentiation. That is, the skin impedance is differentiating the stimulus waveform and therefore the stimulus current. A resistance-capacitance circuit (RC circuit) may be utilized to simulate the bulk resistance and capacitance of the skin-electrode impedance. FIG. 2 is an exemplary schematic circuit for simulating the skin-electrode impedance using an RC circuit. A waveform generator 105 represents the stimulus signal. The stimulus signal produced by waveform generator 105 passes through a series RC circuit (R1 and C1) that represents the bulk resistance and capacitance of the skin to electrode interface. The differentiated current is observed using an oscilloscope 110.

Figure 3:
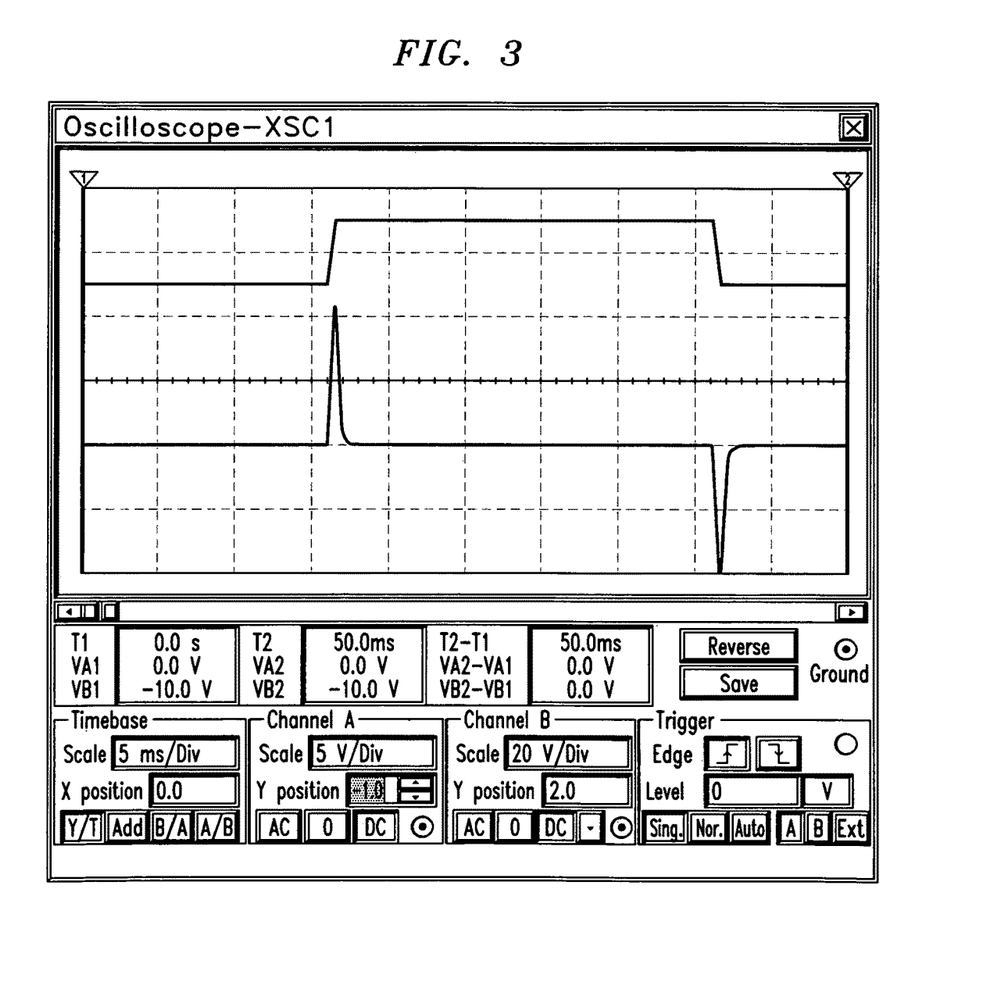
FIG. 3 shows exemplary voltage—time simulation results for the simulated stimulation circuit in FIG. 2 wherein the stimulation waveform is a square wave at a 20 Hz stimulation frequency.
Figure 4:
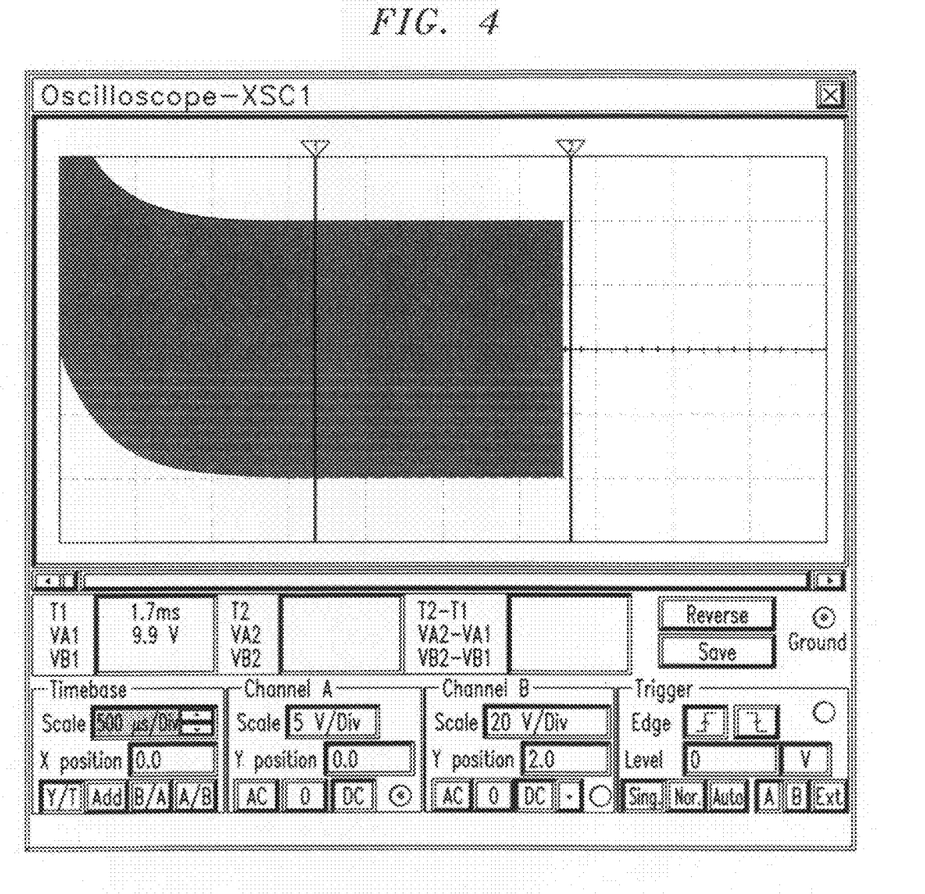
FIG. 4 shows exemplary voltage—time simulation results for the simulated stimulation circuit in FIG. 2 wherein the stimulation waveform is a square wave at a 210 KHz stimulation frequency.

In an illustrative example, the resistance and capacitance values are set to R1=619 Ohms and C1=470 nF, respectively. A voltage—time trace of the simulation results in FIG. 2 is shown in FIG. 3 wherein a square wave stimulus signal is produced by waveform generator 105 at a stimulus frequency of 20 Hz. The top waveform represents the 20 Hz square wave stimulus produced by waveform generator 105 while the lower waveform depicts the differentiated current as observed by oscilloscope 110. The pulse width (duration) of the stimulus signal is approximately 25 ms, whereas the pulse width (duration) of the differentiated current is only approximately 2 ms at both the rising and trailing edges of the stimulus. For the remaining 21 ms of the stimulus pulse, no current is recorded. By way of another example, the square wave stimulus signal produced by waveform generator 105 is set to 210 KHz and the stimulation trace results are shown in FIG. 4. A positive net average current can be seen from time t0 until approximately 600 microseconds. The average current is approximately 0 mA after the initial 600 microseconds. Stimulation beyond 600 microseconds has a zero average current. In the illustrative examples shown in FIGS. 3 and 4, the duration of the differentiated current (Chronaxie) may not be sufficient to activate the intended or target excitable tissue. Thus, it is desirable to increase the duration of the stimulation current in order to fire the action potential of the intended or target excitable tissue.

One possible solution to overcome the loss of stimulus duration due to the skin-electrode impedance is increasing the strength of the stimulus signal above the required Rheobase. Referring once again to the strength—duration waveform in FIG. 1, the stimulus strength required to activate excitable tissue occurring at durations below the Chronaxie are significantly higher values than those occurring above the Chronaxie. Such relatively high stimulus signal strengths may undesirably result in possible activation of a non-targeted tissue. In addition, the increased stimulation signal strength will consume more power which may be disadvantageous especially when the external stimulating device has a limited power supply.

The present inventive system and method compensates for changing or varying skin to electrode impedance as well as the decay in current by widening the decay, i.e., increasing the time, so that the nerve fires without having to increase the power of the device. By increasing the time to allow the stimulus to fire the nerve the decay in current is prolonged. The decay can be widened or increased, in other words more time is added, by either including additional series impedance and/or by increasing the amplitude of the stimulation waveform during the decay.

Figure 5A:
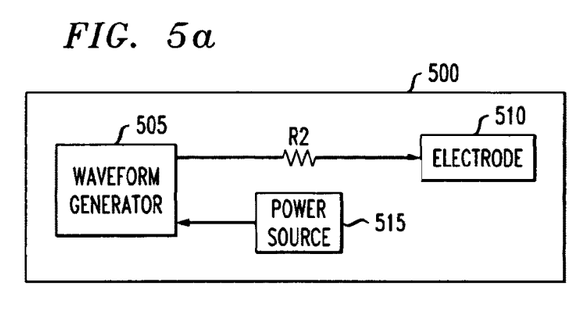
FIG. 5a is an exemplary schematic stimulation circuit compensating for the skin-electrode impedance by adding an in-line series resistor.

It has been recognized that by controlling the impedance of the electrode to skin interface the duration of the stimulus current can be increased or decreased slightly above the Chronaxie of the intended excitable tissue or slightly below the Chronaxie of the unintended excitable tissue. That is, in-line series resistance (R2) can be added on the electrode side of the interface to shift the stimulus pulse duration above the Chronaxie of the intended physiological target (e.g., excitable tissue), as shown in FIG. 5a. For example, a resistance of several hundred ohms may be added to slightly increase the impedance so that the stimulus pulse duration is shifted above the Chronaxie. Conversely, the series resistance (R2) can be removed or instead parallel resistance added (R3)(as represented in FIG. 5d) from the electrode side of the interface to shift the stimulus pulse duration below the Chronaxie of the unintended excitable tissue. In this way, the strength of the stimulus signal may be compensated so that the target or intended tissue is stimulated even if the impedance of the skin changes. It is also contemplated and within the intended scope of the present invention to control the resistance on a real time basis by detecting the impedance of the skin and adjusting a variable in-line series resistor based on the detected impedance. Preferably the impedance of the skin in sampled or monitored in real time and from this measured value is derived the resistance and capacitance (current decay). The impedance of the skin may be measured using conventional schemes such as applying a current source (constant or variable) and measuring the skin impedance using a sensor or electrode place on the surface of the skin. The variable resistance and thus stimulus pulse duration is preferably varied in direct proportion to that of the detected skin-electrode impedance. That is, as the detected skin-electrode impedance increases the variable resistance is increased to lengthen the duration of the stimulus pulse to allow a longer period of time for stimulation, whereas as the impedance decreases the variable resistance is decreased thereby shortening the duration of the stimulus pulse.

Figure 5B:
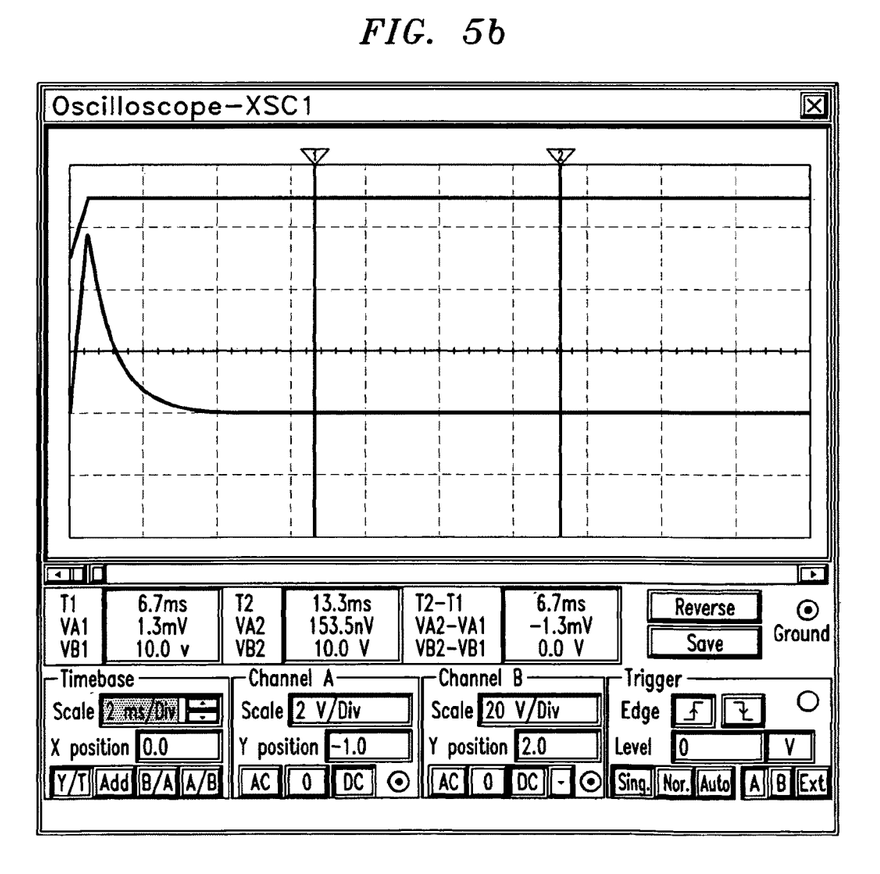
FIG. 5b shows exemplary voltage—time simulation results for the simulated stimulation circuit in FIG. 5a wherein the stimulation waveform is a square wave at 20 Hz stimulation frequency.

FIG. 5b is an exemplary stimulation trace in which a 1 kΩ in-line series resistor R2 was added and the simulation was re-run at 20 Hz. Once again the upper waveform represents the stimulation signal whereas the lower waveform represents the differentiated current. The current pulse of the waveform shown in FIG. 5b is now 3 ms in duration representing an increase of 1 ms from the baseline case with no series resistance in FIG. 2 in which the current pulse waveform was 2 ms in duration.

Figure 5C:
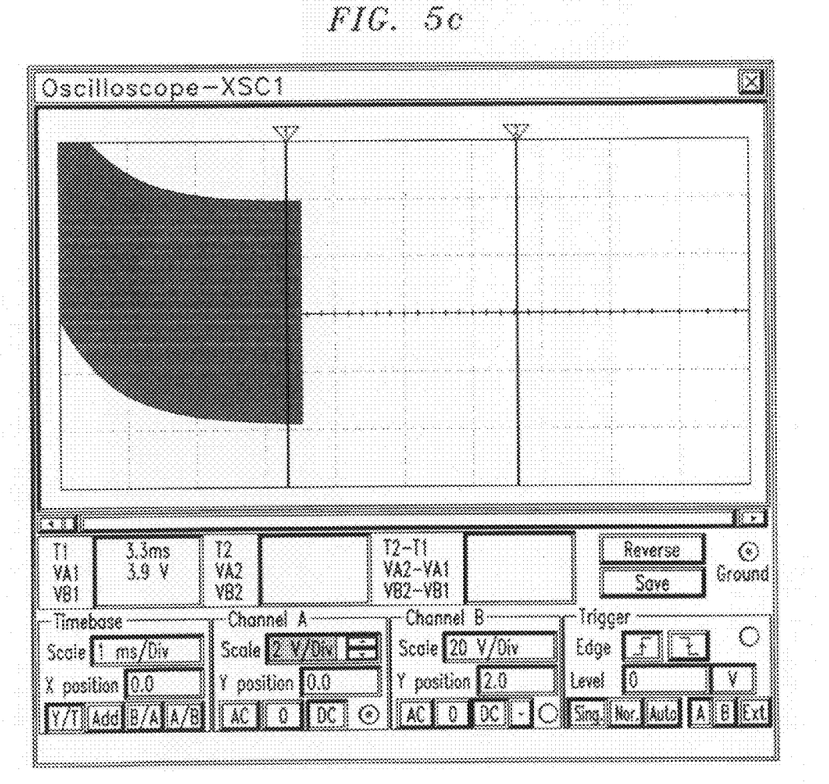
FIG. 5c shows exemplary voltage—time simulation results for the simulated stimulation circuit in FIG. 5a wherein the stimulation waveform is a square wave at 210 KHz stimulation frequency.
Figure 5D:
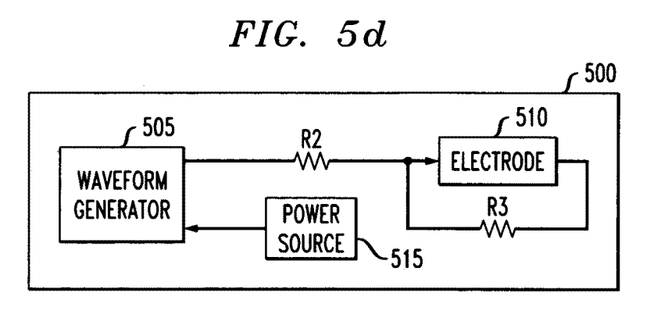
FIG. 5d is an exemplary schematic stimulation circuit compensating for the skin-electrode impedance by adding a parallel resistance.

FIG. 5c shows the trace of the stimulus current waveform at a 210 KHz with the same in-line series resistance of 1 kΩ. A current pulse duration greater than zero can be seen for 2.5 ms representing a 1.9 ms increase above the baseline of 600 microseconds (0.6 ms), which previously represented an average current of approximately 0 mA in FIG. 4. These exemplary stimulus current waveform traces verify that the addition of an in-line series resistor increases the duration of the stimulus pulse to above the threshold for excitation of nerves (in this example 600 microseconds) so that a nerve will be stimulated even if the impedance of the skin changes. To minimize power consumption, preferably the minimum amount of in-line series resistance to achieve excitation of a nerve is used. However, if power consumption is not a factor or consideration of a particular circuit design, the in-line resistance value need not be minimized.

In those circumstances in which power consumption is a consideration such as with a limited power source (e.g., battery) increased impedance via addition of any in-line series resistance will disadvantageously dissipate or consume some power thereby shortening the lifespan of the power source. An alternative method for widening the decay while minimizing the power consumed is to use a waveform for the stimulus signal whose envelope has a non-zero slope or rate of change at least during the current decay. Referring once again to FIG. 3 in which a square wave stimulus signal having a zero slope envelope was used a differentiation current was present for only a very small pulse width (duration) of several milliseconds while for the remainder of the stimulus pulse, no current was present. The slope or rate of change of the stimulus pulse envelope is directly proportional to the duration of non-zero current. It is therefore desirable to employ a stimulus waveform whose envelope has a non-zero slope or rate of change at least during current decay of the waveform to optimize the duration of the non-zero current. Preferably, a stimulus waveform is used whose envelope has a non-zero slope or rate of change over substantially the duration of current decay of the waveform, and most preferably over substantially the entire stimulus pulse width or interval.

Figure 7:
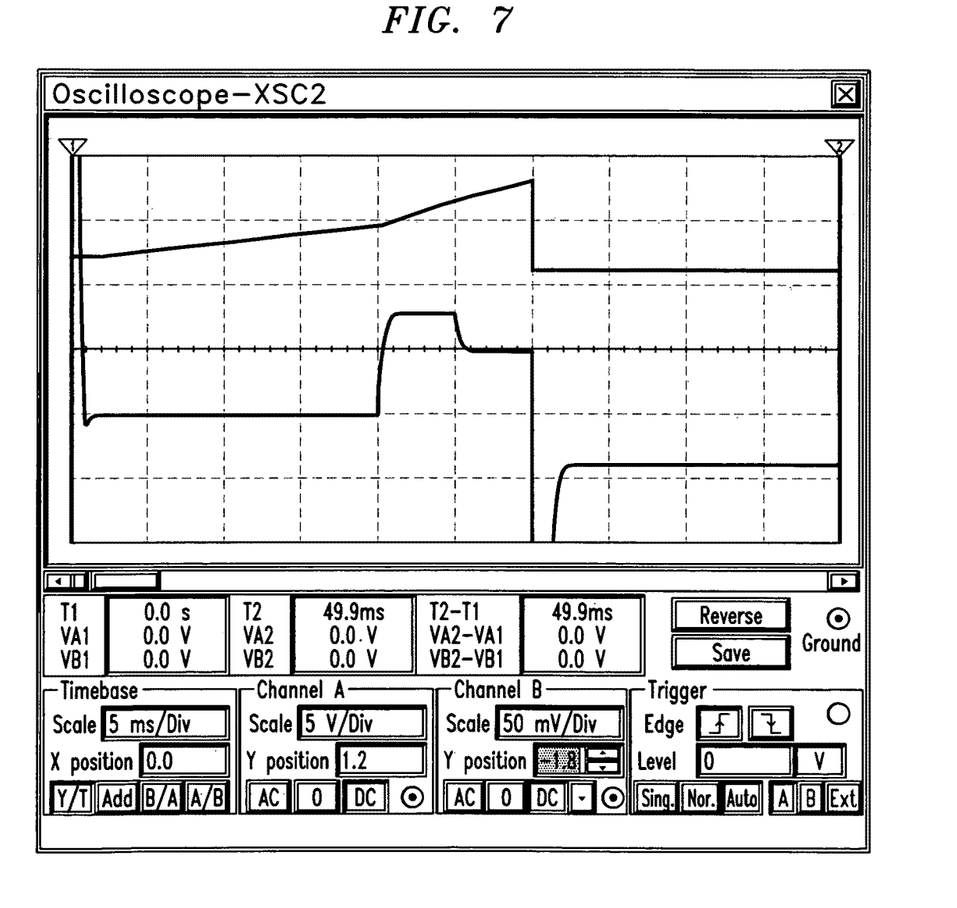
FIG. 7 is an exemplary voltage—time simulation result for the simulated stimulation circuit in FIG. 2 wherein the stimulation waveform is a predetermined ramped waveform.

Instead of a square wave stimulus having zero slope, a few exemplary predetermined waveforms whose envelopes have a non-zero slope or rate change during the current decay were utilized and the results observed. In a first example, a ramped stimulus was employed using the simulation setup in FIG. 2 at a frequency of 20 Hz, the results of which are depicted in FIG. 7. The ramped stimulus is the top trace while the differentiated current trace is the bottom trace. The pulse width (duration) of the ramped stimulus is approximately 30 ms. The duration of non-zero current can be seen for the duration of the stimulus and is proportional to the slope or rate of change of the applied stimulus.

Figure 8:
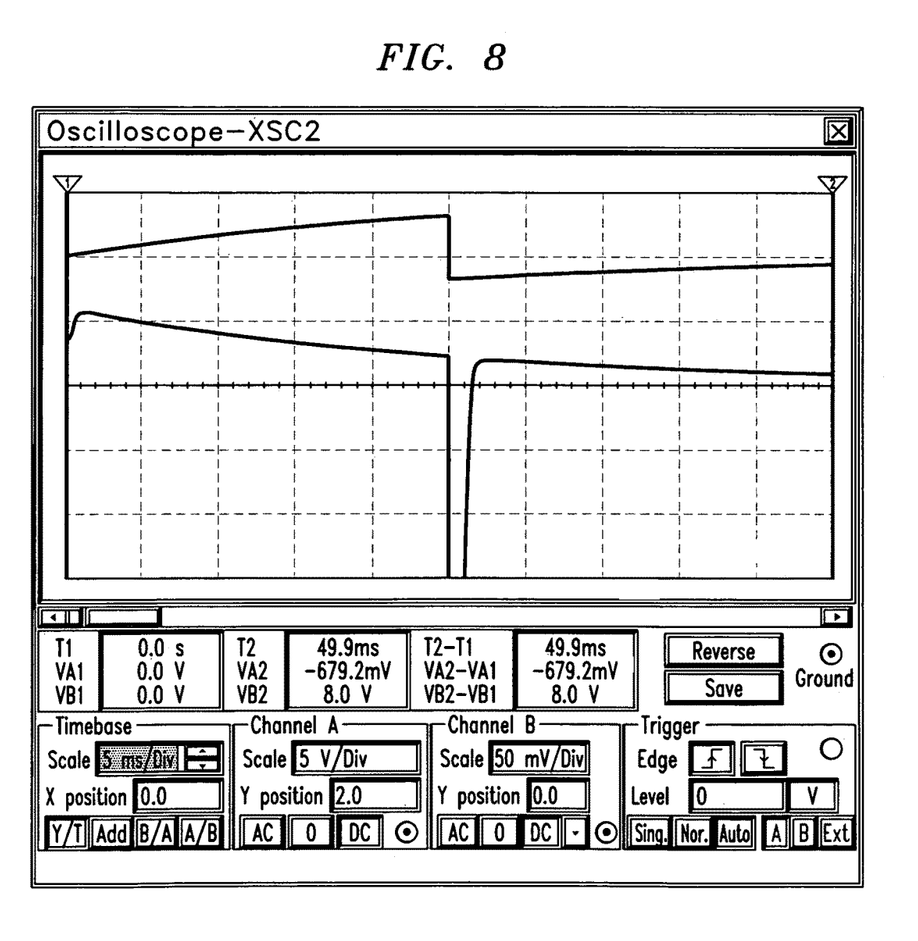
FIG. 8 is an exemplary voltage—time simulation result for the simulated stimulation circuit in FIG. 2 wherein the stimulation waveform is a predetermined exponential waveform.

Yet another example employing an exponential stimulus waveform using the simulation circuitry in FIG. 2 was also run at a frequency of 20 Hz. In FIG. 8, the exponential stimulus is the top trace, while the differentiated current trace is the bottom trace. The pulse width (duration) stimulus is approximately 25 ms. Once again, the duration of non-zero current can be seen for the duration of the stimulus and is proportional to the slope or rate of change of the applied stimulus.

The slope or rate of change of the applied stimulus envelope is preferably selected to match and thus compensate for the skin impedance. Since the skin impedance may vary over time due to any number of factors previously mentioned it would be desirable to adjust the slope or rate of change of the applied stimulus envelope on a real time basis to match the detected capacitance rather than employ a predefined stimulus waveform. Therefore, instead of applying as the stimulation signal a predetermined stimulation envelope whose slope at least during substantially the duration of current decay is non-zero, the slope of the stimulus envelope may be adjusted on a real time basis at least during substantially the duration of current decay to compensate for the monitored skin to electrode impedance. As the detected skin-electrode impedance increases the slope of the envelope is increased to widen the decay thereby allowing a longer duration for stimulation, whereas as the detected skin-electrode impedance decreases the slope of the envelope is decrease thereby shortening the decay and duration for stimulation.

Figure 6:
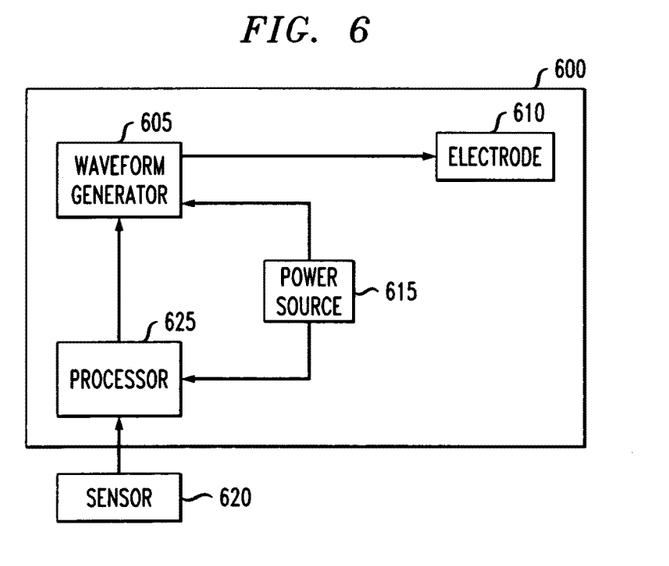
FIG. 6 is an exemplary schematic diagram of a transcutaneous externals stimulation device for adjusting the envelope of the stimulation signal based on feedback of detected skin impedance.

An exemplary schematic diagram of a surface based stimulation device 600 in accordance with the present invention that adjusts the envelope of the stimulation signal waveform on a real time basis as a function of detected skin impedance feedback is shown in FIG. 6. Preferably the impedance of the skin in sampled or monitored in real time and from this measured value is derived the resistance and capacitance (current decay). The impedance of the skin may be measured using conventional schemes such as applying a current source (constant or variable) and measuring the skin impedance using a sensor 620 or electrode placed on the surface of the skin. Depending on the amount or intensity of the monitored decay, the surface based stimulation device includes a processor or controller 625 powered by a power source 615 and programmed to adjust during the current decay the shape of the waveform (e.g., slope of the pulse envelope) produced by the waveform generator 605 in real time to compensate for this measured current decay. The adjusted current stimulus produced by the waveform generator 605 is received as input to the external electrode 610 to stimulate the target (e.g., nerve).

Therefore, the stimulus signal may be compensated for skin electrode impedance by adding/eliminating an in-line series resistance or by changing the shape of the envelope of the stimulus waveform so that its average current is non-zero during current decay. It is also contemplated and within the intended scope of the present invention for these two options to be utilized simultaneously to compensate for any variation in the stimulation current due to impedance of the skin.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for ensuring firing of an action potential in an intended physiological target activated by a stimulus pulse generated by an electrode of a non-invasive surface based stimulation device irrespective of skin-to-electrode impedance, comprising the steps of:
    sensing the skin-to-electrode impedance;
    deriving from the sensed skin-to-electrode impedance a current decay; detecting a strength-duration curve of the intended physiological target and a Chronaxie in the strength-duration curve of the intended physiological target;
    detecting based on the Chronaxie in the strength-duration curve of the intended physiological target when the derived current decay is insufficient to fire the action potential in the intended physiological target;
    increasing internal impedance of the stimulation device; and
    generating the stimulus pulse using the electrode;
    wherein the increased internal impedance widens a duration of the stimulus pulse so as to ensure firing of the action potential of the intended physiological target irrespective of the sense skin-to-electrode impedance.

2. The method in accordance with claim 1, wherein the increasing step comprises the step of shifting the duration of the stimulus pulse above the Chronaxie of the intended physiological target required for firing of the action potential.

3. The method in accordance with claim 1, wherein the increasing step comprises adding a resistor in series with the electrode.

4. The method in accordance with claim 3, further comprising the step of in the presence of a reduction in the sensed skin-to-electrode impedance, decreasing the internal impedance by removing the series resistor.

5. The method in accordance with claim 3, in the presence of a reduction in the sensed skin-to-electrode impedance, further comprising the step of decreasing the internal impedance by adding a parallel resistor across the electrode.

6. The method in accordance with claim 3, wherein the resistor is several hundred ohms.

7. The method in accordance with claim 1, wherein the step of generating the stimulus pulse comprises the steps of:
    generating a stimulation waveform that optimizes a non-zero average current during current decay of the stimulus pulse; and
    producing the stimulus pulse using the electrode that receives as input the stimulation waveform;
    wherein the increased internal impedance widens the duration of the stimulus pulse by using the stimulation waveform that optimizes the non-zero average current during current decay of the stimulus pulse without the addition of an in-line series resistance.

8. The method in accordance with claim 7, wherein the step of generating the stimulation waveform comprises selecting the stimulation waveform forming an envelope having a non-zero slope during at least a portion of the current decay.

9. The method in accordance with claim 8, wherein the non-zero slope of the envelope of the stimulation waveform extends over approximately 50% of the current decay.

10. The method in accordance with claim 9, wherein the non-zero slope of the envelope of the stimulation waveform extends over substantially the entire current decay.

11. The method in accordance with claim 7, wherein the stimulation waveform is a predefined waveform.

12. The method in accordance with claim 11, wherein the predefined waveform is one of a ramp or an exponential waveform.

13. The method in accordance with claim 7, wherein the skin-to-electrode impedance is sensed in real time.

14. The method in accordance with claim 13, wherein the producing step comprises the step of adjusting in real time during the current decay the slope of the stimulation waveform so as to substantially match the sensed real time skin-to-electrode impedance.

15. The method in accordance with claim 14, wherein the adjusting step comprises increasing the slope of the envelope of the stimulation waveform as the sensed real time skin-to-electrode impedance increases, while decreasing the slope of the envelope of the stimulation waveform as the sensed real time skin-to-electrode impedance decreases.

* * * * *